(12) United States Patent
Kondo et al.

(10) Patent No.: US 8,834,691 B2
(45) Date of Patent: Sep. 16, 2014

(54) DEVICE FOR MEASURING BIOLOGICAL SAMPLE

(75) Inventors: Reiko Kondo, Ehime (JP); Takashi Miki, Ehime (JP); Atsushi Watanabe, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 14/001,954

(22) PCT Filed: Mar. 28, 2012

(86) PCT No.: PCT/JP2012/002155
§ 371 (c)(1),
(2), (4) Date: Aug. 28, 2013

(87) PCT Pub. No.: WO2012/132432
PCT Pub. Date: Oct. 4, 2012

(65) Prior Publication Data
US 2013/0334041 A1   Dec. 19, 2013

(30) Foreign Application Priority Data
Mar. 28, 2011   (JP) .................. 2011-069226

(51) Int. Cl.
| | | |
|---|---|---|
| *G01N 27/327* | (2006.01) | |
| *G01N 33/487* | (2006.01) | |
| *C12Q 1/54* | (2006.01) | |
| *A61B 5/157* | (2006.01) | |
| *A61B 5/145* | (2006.01) | |
| *A61B 5/151* | (2006.01) | |
| *C12Q 1/00* | (2006.01) | |
| *G01N 33/64* | (2006.01) | |
| *G01N 33/66* | (2006.01) | |

(52) U.S. Cl.
CPC .............. *G01N 27/327* (2013.01); *C12Q 1/006* (2013.01); *G01N 33/64* (2013.01); *G01N 2333/904* (2013.01); *C12Q 1/54* (2013.01); *G01N 33/66* (2013.01); *G01N 33/4875* (2013.01); *A61B 5/14532* (2013.01); *A61B 5/15126* (2013.01)

USPC .................. 204/403.01; 422/68.1; 422/82.01; 435/287.1; 600/347; 600/309

(58) Field of Classification Search
CPC ..... G01N 33/64; G01N 33/66; G01N 33/487; G01N 2333/904; G01N 27/26; G01N 27/3273; C12Q 1/006; C12Q 1/54; A61B 5/157; A61B 5/145; A61B 5/151
USPC ............. 204/403.01–403.15; 422/82.01, 68.1
See application file for complete search history.

(56) References Cited

U.S. PATENT DOCUMENTS

| | | | |
|---|---|---|---|
| 2006/0091006 A1 | 5/2006 | Wang et al. | |
| 2008/0125700 A1* | 5/2008 | Moberg et al. | .................. 604/67 |
| 2011/0257496 A1* | 10/2011 | Terashima et al. | ............ 600/347 |

FOREIGN PATENT DOCUMENTS

| | | |
|---|---|---|
| CN | 102197304 A | 9/2011 |
| EP | 1 382 968 A1 | 1/2004 |

(Continued)

OTHER PUBLICATIONS

International Search Report for PCT/JP2012/002155 dated Apr. 24, 2012.

(Continued)

*Primary Examiner* — Jennifer Dieterle
(74) *Attorney, Agent, or Firm* — Pearne & Gordon LLP

(57) ABSTRACT

The objective of the invention is to enhance measurement accuracy in a device for measuring a biological sample. To attain this objective, the invention is provided with a main case (2) having a sensor insertion section (1), a measurement section (7) connected to the sensor insertion section (1), a controller (8) connected to the measurement section (7), and a display (3) connected to the controller (8). An acceleration sensor (5) is furnished for detecting a shock applied to the sensor insertion section (1).

20 Claims, 19 Drawing Sheets

(56) References Cited

FOREIGN PATENT DOCUMENTS

| | | |
|---|---|---|
| JP | 2000-283789 A | 10/2000 |
| JP | 2010-266217 A | 11/2010 |
| WO | 02/44705 A1 | 6/2002 |
| WO | 2010/052849 A1 | 5/2010 |

OTHER PUBLICATIONS

English translation of the Search Report for the Chinese Patent Application No. 201280006779.7 dated Jun. 12, 2014.
Supplementary European Search Report for Application No. EP 12 76 5681 dated Jul. 11, 2014.

* cited by examiner

ERROR HAS BEEN CAUSED
DURING MEASUREMENT!
REPLACE SENSOR WITH NEW ONE
AND MAKE MEASUREMENT AGAIN.
NOTE THAT SPOT APPLICATION
MUST BE CARRIED OUT SLOWLY.

ERROR HAS BEEN CAUSED
DURING MEASUREMENT!
REPLACE SENSOR WITH NEW ONE
AND MAKE MEASUREMENT AGAIN.
NOTE THAT IMPACT MUST NOT BE APPLIED
TO METER DURING MEASUREMENT!!

DEVICE FOR MEASURING BIOLOGICAL SAMPLE

TECHNICAL FIELD

The present invention relates to a biological sample measuring apparatus, and particularly to a biological sample measuring apparatus for measuring blood glucose levels, for example.

BACKGROUND ART

A conventionally a biological sample measuring apparatus includes a main body case having a sensor insertion section, a measurement section connected to the sensor insertion section, a control section connected to the measurement section, and a display section connected to the control section (see, PTL 1, for example).

Specifically, in the conventional biological sample measuring apparatus, when blood is spotted on a blood glucose level sensor inserted in the sensor insertion section, blood glucose level is measured by a measurement section, and the measured blood glucose level is displayed on the display section.

CITATION LIST

Patent Literature

PTL 1
WO02/044705

SUMMARY OF INVENTION

Technical Problem

A problem with the conventional biological sample measuring apparatuses lies in that the measurement accuracy may be low in some cases. Specifically, in the conventional biological sample measuring apparatus, when blood is spotted on a blood glucose level sensor inserted in the sensor insertion section, the blood reaches a reaction reagent, causing electro chemical reactions. Then, by observing the states of the electrochemical reactions using the measurement section, blood glucose level is detected. However, when an impact is applied to the blood glucose level sensor after the spotting of blood on the blood glucose level sensor but before the completion of the measurement, the blood may not be allowed to smoothly reach a reagent portion, and as a result, the measurement accuracy may be lowered.

Such an impact tends to be caused when separating a finger from the blood glucose level sensor at the time of spot application of blood exuded from the punctured finger on the blood glucose level sensor. Specifically, in such a situation that the blood glucose level sensor is flicked by the finger, the spotted blood fails to smoothly reach the reaction reagent because of the impact thus caused, and as a result, the measurement accuracy is lowered.

Under such circumstances, an object of the present invention is to improve the measurement accuracy of a biological sample measuring apparatus.

Solution to Problem

In order to achieve the above-mentioned object, the present invention provides a biological sample measuring apparatus including: a main body case including a sensor insertion section; a measurement section connected to the sensor insertion section; a control section connected to the measurement section; and a display section connected to the control section, wherein an acceleration sensor that detects an impact applied to the sensor insertion section is provided. Thus, the desired object is achieved.

Advantageous Effects of Invention

With the biological sample measuring apparatus according to the present invention, the measurement accuracy can be improved. Specifically, in the present invention, for example, when an impact is applied to the sensor insertion section via the biological sample measuring sensor for measuring blood glucose levels and the like, the impact thus applied is detected by the acceleration sensor. Then, when the impact level is greater than a predetermined value, it is possible to display, on the display section, the fact that the measurement result measured by the measurement section is inadequate. Thus, inadequate measured values are not displayed, and the measurement accuracy is improved.

DESCRIPTION OF EMBODIMENTS

In the following, an embodiment of the present invention which is applied to a biological sample measuring apparatus for measuring blood glucose levels is described with reference to the accompanying drawings.

Embodiment 1

Figure 1:
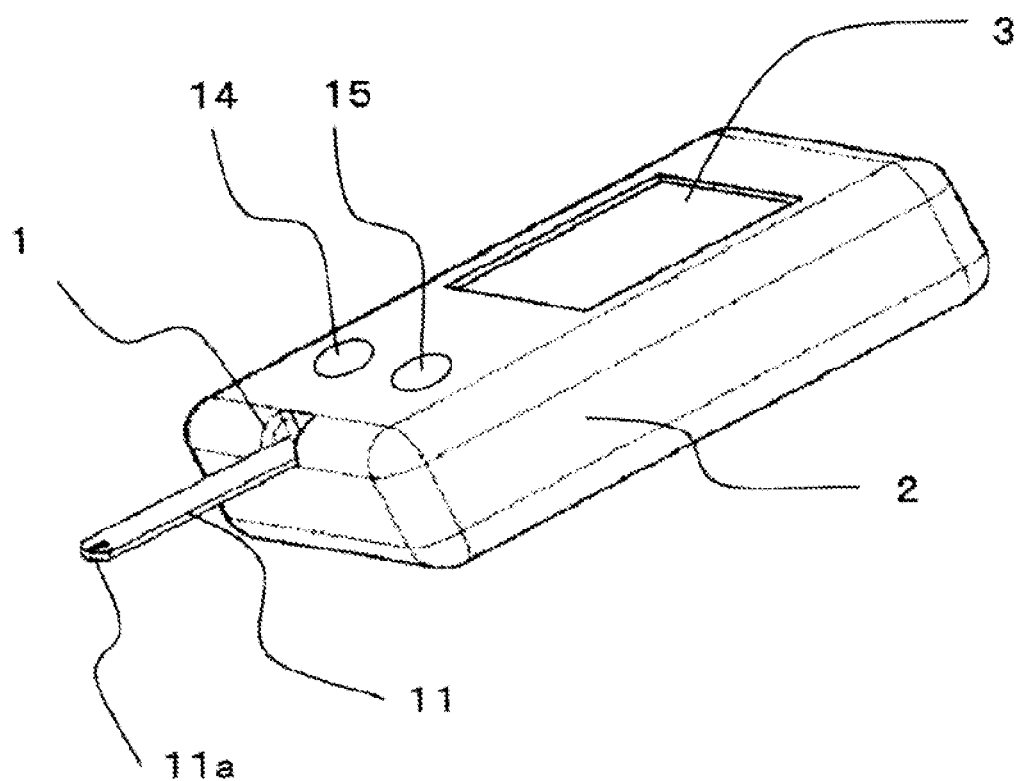
FIG. 1 is a perspective view of a biological sample measuring apparatus according to Embodiment 1.
Figure 2:
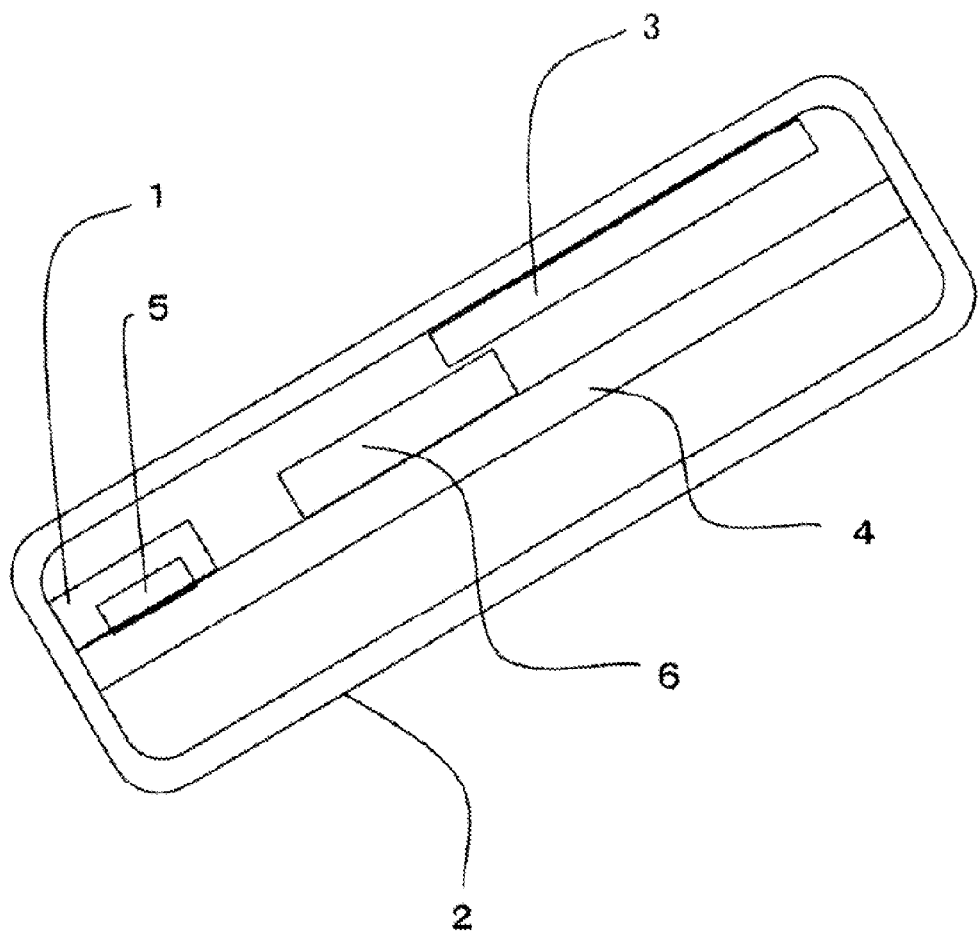
FIG. 2 is a sectional view of the biological sample measuring apparatus illustrated in FIG. 1.
Figure 3:
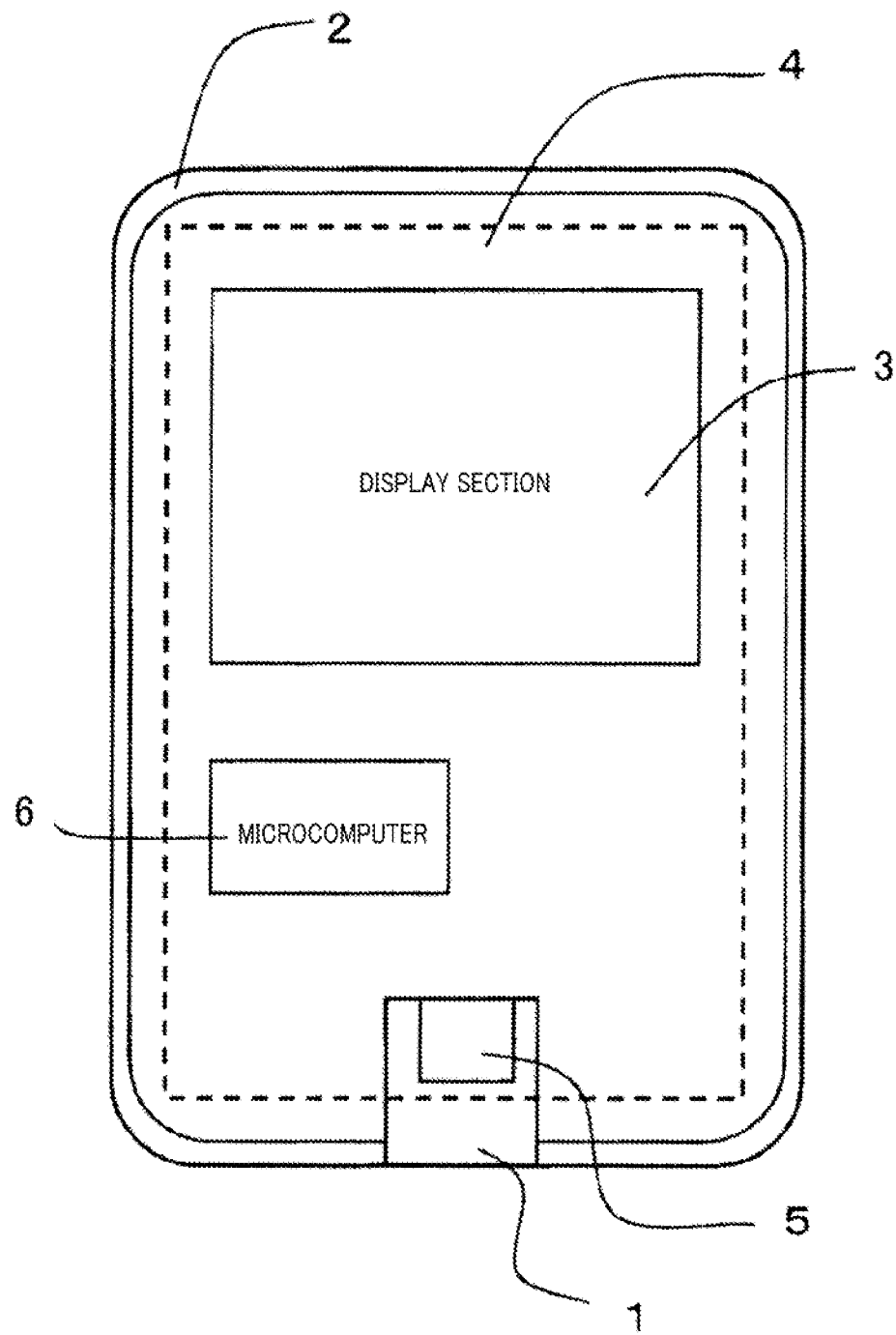
FIG. 3 is a plan view of the biological sample measuring apparatus illustrated in FIG. 1.
Figure 4:
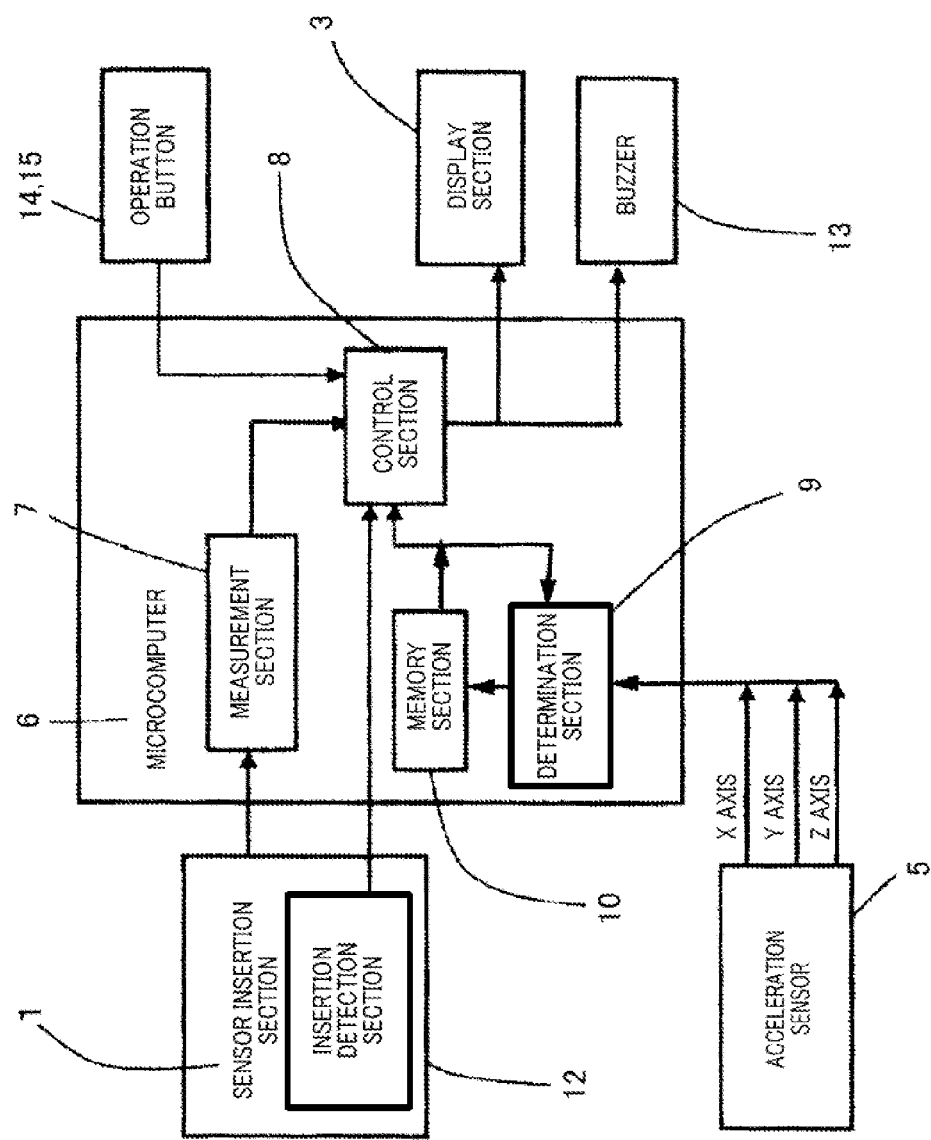
FIG. 4 is a control block diagram of the biological sample measuring apparatus illustrated in FIG. 1.

FIG. 1 is a perspective view of a biological sample measuring apparatus of the present embodiment; FIG. 2 is a sectional view thereof; FIG. 3 is a top view thereof; and FIG. 4 is a control block diagram thereof. As illustrated in FIG. 1, the biological sample measuring apparatus of the present embodiment includes main body case 2 having sensor insertion section 1 at one end thereof. In sensor insertion section 1, sensor 11 having spot application section 11a is provided for insertion.

Display section 3, and operation buttons 14 and 15 are provided on the upper surface of main body case 2. As illustrated in FIG. 2, sensor insertion section 1 is disposed at an end of substrate (electric circuit substrate) 4 provided in main body case 2. In addition, acceleration sensor 5 is disposed in sensor insertion section 1 as illustrated in FIG. 2 and FIG. 3.

Inside sensor insertion section 1, a connector section (not illustrated) that electrically connects with biological sample measuring sensor 11 inserted thereto is provided. When biological sample measuring sensor 11 is inserted in sensor insertion section 1, a measurement section configured on substrate 4 and the connecting section of biological sample measuring sensor 11 are electrically connected to each other via the connector section.

It is desirable that acceleration sensor 5 be disposed at a position adjacent to the connector section. Thus, acceleration sensor 5 is disposed on substrate 4 in the proximity of control device 6; in other words, acceleration sensor 5 is disposed on substrate 4 in the proximity of control device 6 functioning as a measurement section or control section. In addition, acceleration sensor 5 is disposed in the proximity of sensor insertion section 1.

Control device 6 which is called the microcomputer is disposed on the upper surface of substrate 4. As illustrated in FIG. 4, control device 6 includes measurement section 7 connected to sensor insertion section 1, control section 8 connected to measurement section 7, determination section 9 connected to acceleration sensor 5, and memory section 10 connected to determination section 9. Determination section 9 and memory section 10 are connected to control section 8.

In addition, sensor insertion section 1 is provided with insertion detection section 12 for detecting insertion of biological sample measuring sensor 11, and insertion detection section 12 is connected to control section 8. Further, display section 3, buzzer 13 as an example of alarm means, and operation buttons 14 and 15 are connected to control section 8.

Figure 5:
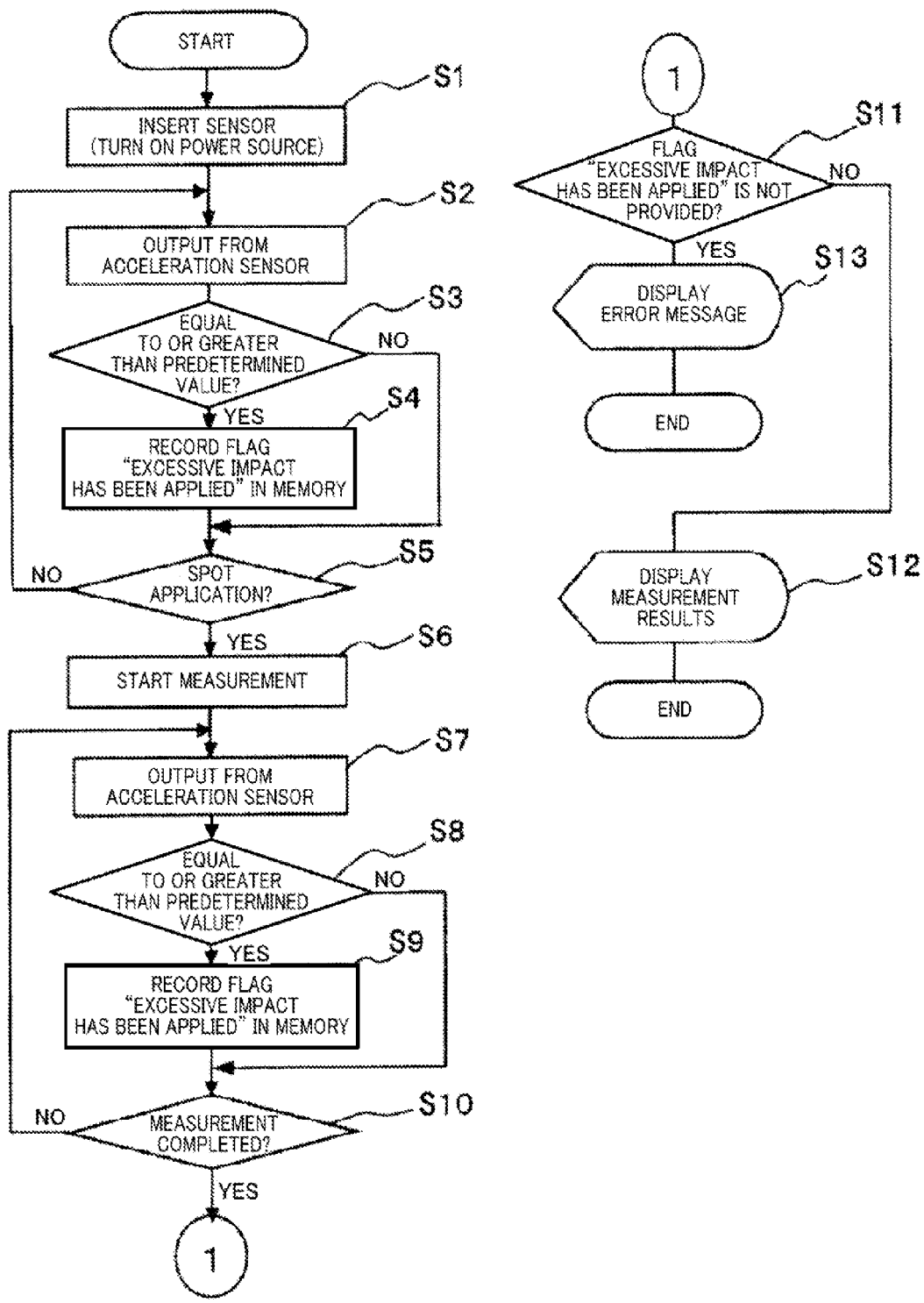
FIG. 5 is a flowchart explanatory of a measurement in the biological sample measuring apparatus illustrated in FIG. 1.

The flow of measuring blood glucose levels by a biological sample measuring apparatus having the above-mentioned configuration is described with reference to FIG. 5. First, a basic measurement flow is described. To make measurement, firstly, biological sample measuring sensor 11 (blood glucose level sensor) is inserted in sensor insertion section 1 as illustrated in FIG. 1. When insertion detection section 12 detects insertion of the sensor, power source is turned on (step S1 in FIG. 5). Thereafter, blood exuded from the punctured finger is spotted on spot application section 11a of biological sample measuring sensor 11 in the state illustrated in FIG. 1 (step S5 in FIG. 5). The spotted blood reaches a reagent (not illustrated) in biological sample measuring sensor 11 from spot application section 11a, and the blood and the reagent causes electrochemical reactions. The signal of the chemical reaction thus caused is measured at measurement section 7 (S10 in FIG. 5), and the results of the measurement are displayed on display section 3 (S12 in FIG. 5).

Further, in the present embodiment, whether an excessive impact is applied on sensor insertion section 1 or not is detected between the above-described steps S1 and S5, and between the above-described steps S5 and S10. To be more specific, at S2 (before the measurement) and/or S7 (during the measurement) in FIG. 5, an output from acceleration sensor 5 is input to determination section 9. Then, determination section 9 determines whether or not the value of the output is equal to or greater than a predetermined value (step S3 and/or S8). When the impact determined by determination section 9 is smaller than the predetermined value, it is determined that there is no problem and the process is advanced to step S5 or step S10. Meanwhile, when the impact determined by determination section 9 is equal to or greater than the predetermined value, a flag indicating that "excessive impact has been applied" is recorded in memory section 10 at step S4 or step S9.

After the measurement is completed at step S10, control section 8 determines at step S11 whether the flag has been input to memory section 10 or not. When the flag is found, an error message is displayed on display section 3. An error warning may also be given using buzzer 13 together with the display.

Figures 6A, 6B, 6C, 6D:
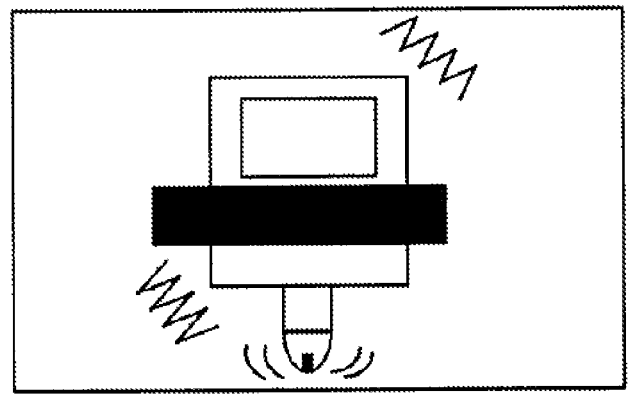
FIGS. 6A to 6D illustrate exemplary error messages displayed by the biological sample measuring apparatus illustrated in FIG. 1.

FIGS. 6A to 6D illustrate exemplary error messages to be displayed on display section 3. FIG. 6A is an error message using a dot matrix pattern to illustrate the fact that an impact has been applied; FIG. 6B is an error message using an error code (in a case of a segment display) to illustrate the fact that an impact has been applied. FIG. 6C and FIG. 6D will be described in Embodiment 3.

At the time of the spot application of blood exuded from a punctured finger on spot application section 11a of biological sample measuring sensor 11, an excessive impact tends to be applied to sensor insertion section 1 when separating the finger from biological sample measuring sensor 11. Specifically, at this time, the finger may accidentally flick spot application section 11a of biological sample measuring sensor 11. Due to the impact caused by the flicking of the finger, the spotted blood is not allowed to smoothly reach a reagent portion in biological sample measuring sensor 11. As a result, the measurement accuracy is lowered.

In view of the foregoing, in the present embodiment, an excessive impact applied to sensor insertion section 1 is detected by acceleration sensor 5. When an excessive impact is detected, an error message is displayed on display section 3. Thus, inadequate measured values are prevented from being displayed. In this manner, the measurement accuracy is increased in the present embodiment.

In the present embodiment, in order to detect an excessive impact applied to sensor insertion section 1 by acceleration sensor 5, acceleration sensor 5 is disposed in sensor insertion section 1 as illustrated in FIG. 3. To be more specific, acceleration sensor 5 is mounted on substrate 4 in sensor insertion section 1.

Acceleration sensor 5 is preferably a three-dimensional acceleration sensor. Three-dimensional acceleration sensors can measure acceleration components in axial directions X, Y and Z. Therefore, when three-dimensional acceleration sensors are used, the direction and amount of the impact can be recorded, and the impact received at sensor insertion section 1 can be grasped in more detail.

Examples of three-dimensional acceleration sensors (or triaxial acceleration sensors) include piezoresistive acceleration sensors, capacitive acceleration sensors, thermal detection acceleration sensors, and the like. Three-dimensional acceleration sensors are applied to mobile phones, game controllers, vibration detection of hard disks, posture control of robots, and the like.

Three-dimensional piezoresistive acceleration sensors include a diaphragm which is formed by forming a thin circular surface using manufacturing technology of silicon semiconductors. In three-dimensional piezoresistive acceleration sensors, a spindle at the center is supported by the thin metal in order to readily detect the displacement caused by acceleration, the locational change of the diaphragm is detected by a piezoresistance device, and amplification and measurement are performed by an electric circuit. Three-dimensional capacitive acceleration sensors detect a slight change in position of a minute movable part supported by a beam structure as a change in capacitance, and perform amplification and measurement by using an electric circuit. Three-dimensional thermal detection acceleration sensors generate a thermal air current in an acceleration sensor housing by using a heater, and use a thermal resistance and the like to detect change of the convection caused by acceleration.

The acceleration sensor used herein is a three-dimensional capacitive acceleration sensor which has a measurement range from −2 g to +2 g (g: gravitational acceleration), for example. The standard gravitational acceleration is 1.0 G=approximately 9.8 m/s$^2$.

Further, it is also possible to compare the impact detected by the acceleration sensor and the durability of main body case 2 and the like, and, as necessary, issue an notification to urge the user to replace the biological sample measuring apparatus as soon as possible. Here, "the durability of main body case 2" is a durability corresponding to the quality assurance range of the mechanical strength for the measuring apparatus, which is assessed based on a mechanical strength test of a main body case (for example, a drop test of the measuring apparatus and the like) in the quality assessment or shipping inspection of measuring apparatuses. To be more specific, the mechanical strength test is a test for determining whether the performance of the measuring apparatus is influenced by factors such as coming off of a component mounted to a substrate in the measuring apparatus, cracks in a substrate or the like, and breakage of a component itself when a drop test of the measuring apparatus as a completed product is performed (for example, a test in which an apparatus is dropped to the floor from heights of 1 m).

Embodiment 2

Figure 7:
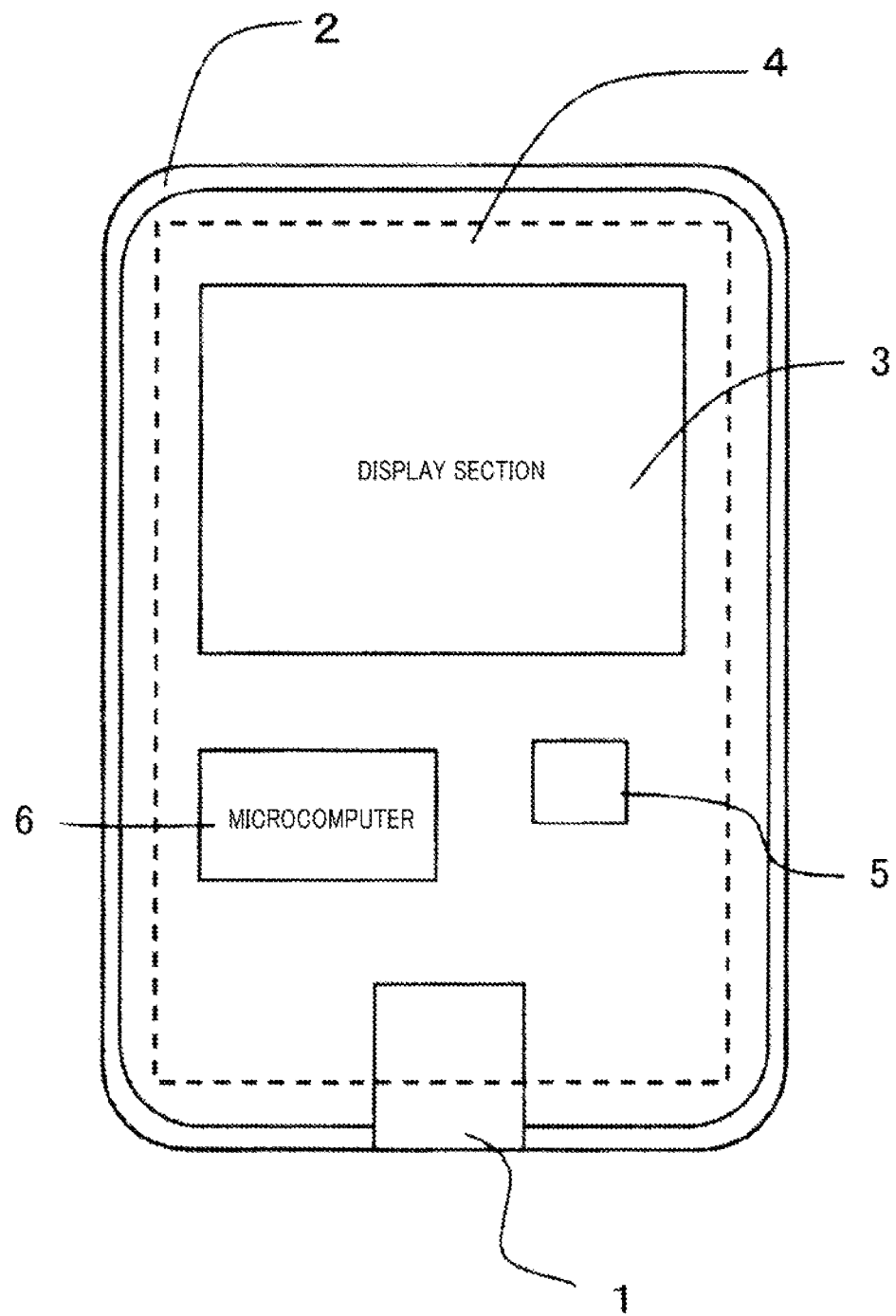
FIG. 7 is a plan view of a biological sample measuring apparatus according to Embodiment 2.

As illustrated in FIG. 7, acceleration sensor 5 of a biological sample measuring apparatus of the present embodiment is disposed on substrate 4 inside main body case 2. Mainly, acceleration sensor 5 disposed as described above can detect the impact applied to the entire main body case 2. For example, an impact is possibly applied to the entire main body case 2 when main body case 2 is dropped during the measurement, or when main body case 2 is carelessly hit against surrounding objects.

Embodiment 3

Figure 8:
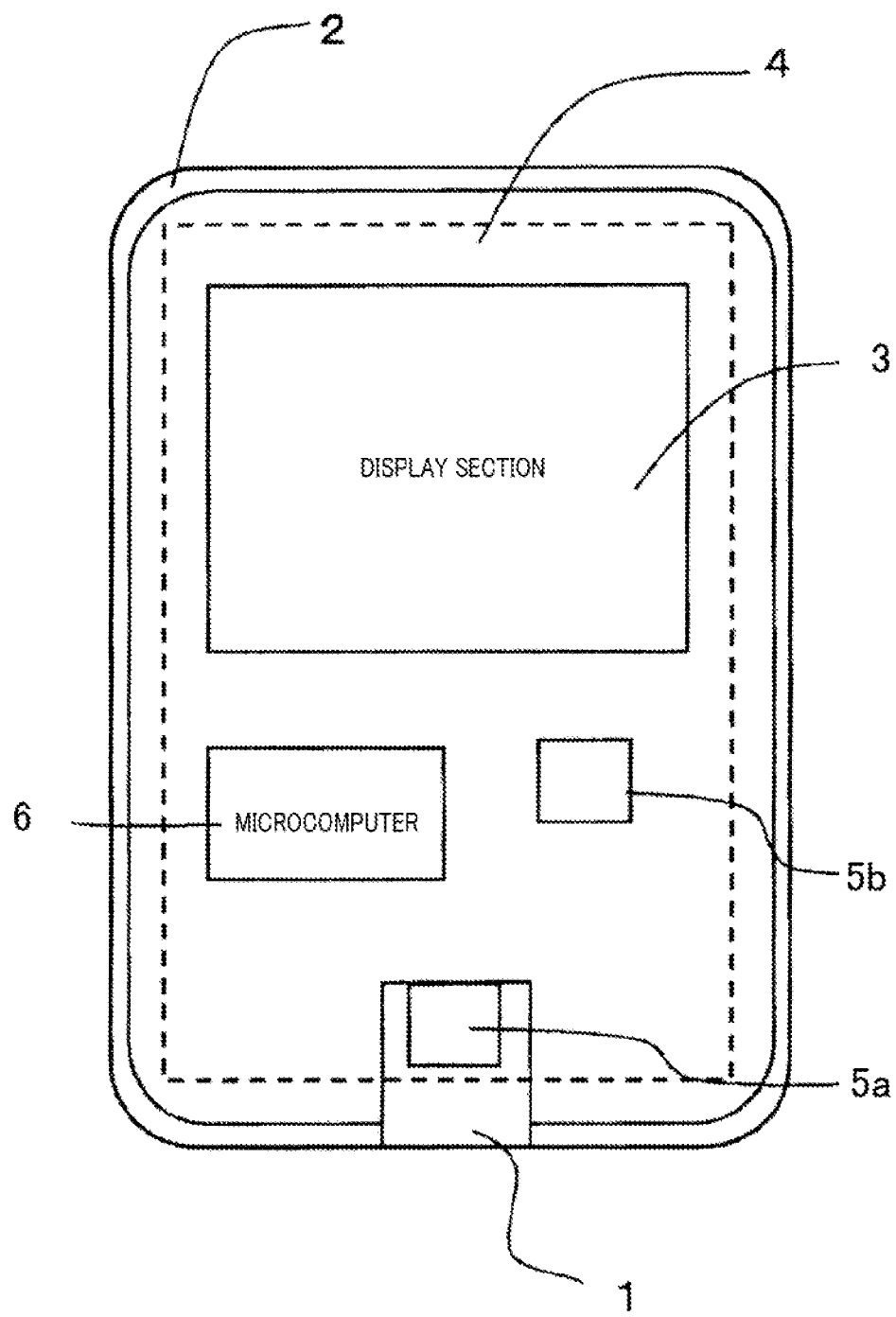
FIG. 8 is a plan view of a biological sample measuring apparatus according to Embodiment 3.

As illustrated in FIG. 8, a biological sample measuring apparatus of the present embodiment includes two acceleration sensors 5a and 5b. Acceleration sensor 5a is provided at a location corresponding to sensor insertion section 1 of substrate 4 as in the case of Embodiment 1. Acceleration sensor 5b is provided on substrate 4 inside main body case 2 as in the case of Embodiment 2.

In the present embodiment, two acceleration sensors 5a and 5b are provided at different locations, and thus the kinds of impact can be detected in detail by utilizing both of the detection results obtained by respective acceleration sensors. Consequently, the reliability of the measurement can be further increased.

To be more specific, acceleration sensor 5a can detect the impact and the like caused by a finger flicking the biological sample measuring sensor 11 at the time of the spot application of blood on spot application section 11a of biological sample measuring sensor 11 installed in sensor insertion section 1. In addition, acceleration sensor 5a can detect the impact applied to the entire main body case 2. On the other hand, acceleration sensor 5b can detect the impact applied to the entire main body case 2 since acceleration sensor 5b is disposed in main body case 2 at substantially the center thereof, but acceleration sensor 5b is insufficient to detect the impact caused by the flicking of biological sample measuring sensor 11.

In view of the foregoing, when only acceleration sensor 5a has detected an impact greater than a predetermined value, it is determined that biological sample measuring sensor 11 is flicked by the user's finger at the time of the spot application. Then, the error message illustrated in FIG. 6C is displayed on display section 3. Meanwhile, when each of acceleration sensors 5a and 5b has detected an impact greater than a predetermined value, it is determined that the impact is applied to the entire main body case 2, and then the error message illustrated in FIG. 6D is displayed on display section 3 to call the user's attention.

Embodiment 4

Figure 9:
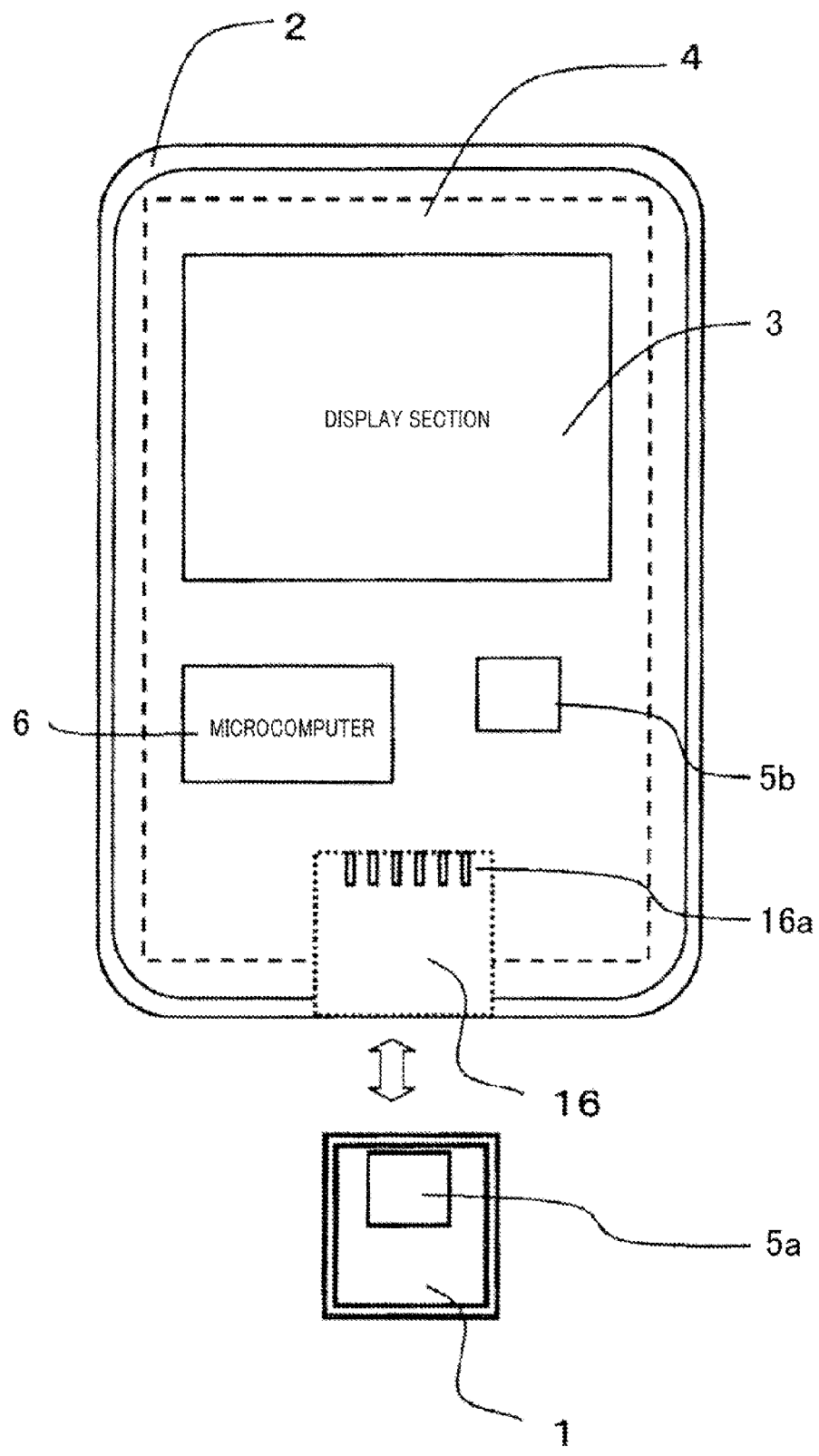
FIG. 9 is a plan view of a biological sample measuring apparatus according to Embodiment 4.
Figure 10:
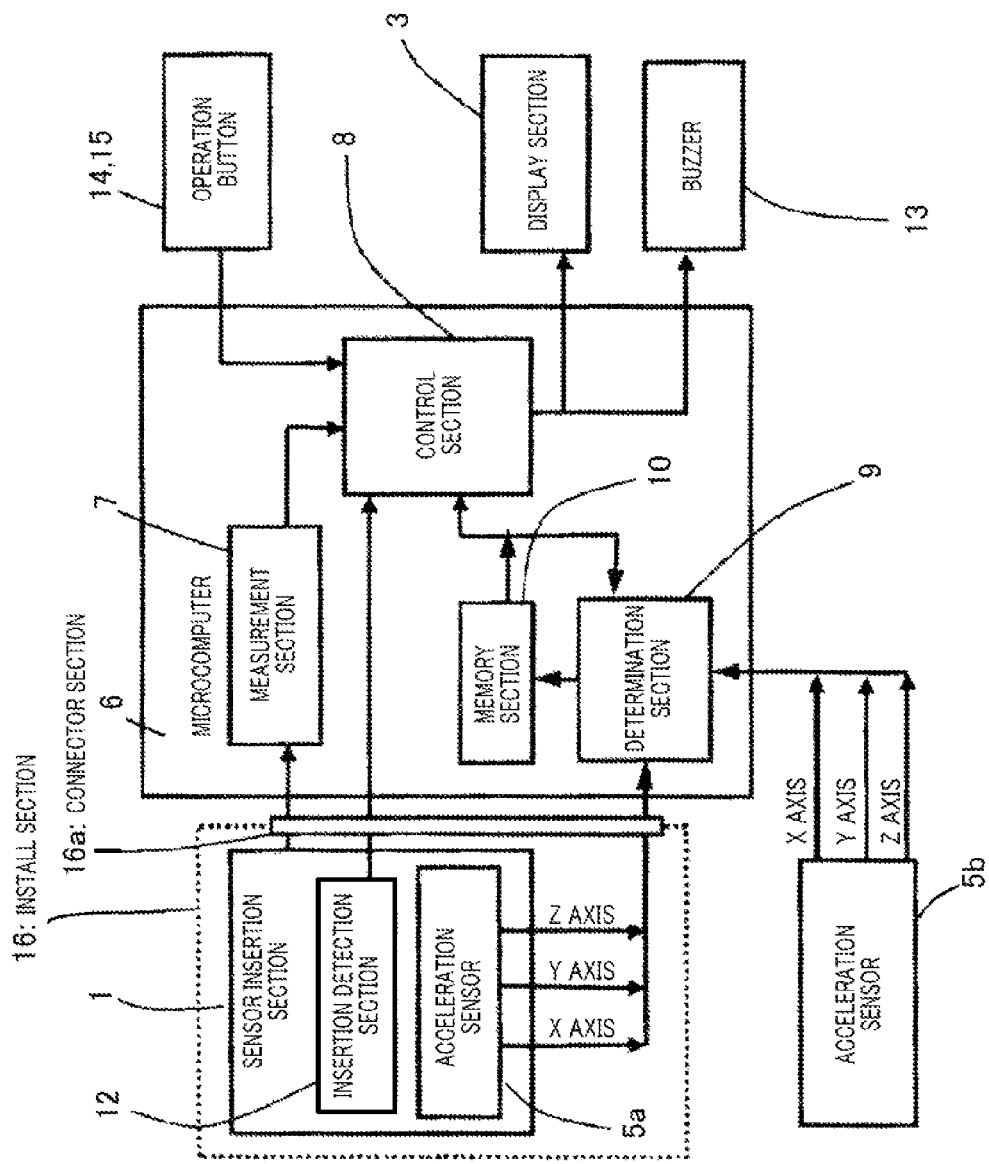
FIG. 10 is a control block diagram of the biological sample measuring apparatus illustrated in FIG. 9.

In a biological sample measuring apparatus of the present embodiment, while two acceleration sensors are incorporated as in the case of Embodiment 3, sensor insertion section 1 is detachably provided in main body case 2 as illustrated in FIG. 9 and FIG. 10. Specifically, the biological sample measuring apparatus of the present embodiment includes main body case 2 provided with acceleration sensor 5b and install section 16, and sensor insertion section 1 provided with acceleration sensor 5a and insertion detection section 12. And sensor insertion section 1 can be detachably installed in install section 16.

As illustrated in FIG. 9, install section 16 is provided with connector section 16a having a plurality of connection terminals. As illustrated in FIG. 10, when sensor insertion section 1 is installed in install section 16, signals of acceleration sensor 5a and insertion detection section 12 which configure sensor insertion section 1 are transmitted via connector section 16a to determination section 9 and control section 8 which are included in control device 6 disposed on substrate 4 in main body case 2.

When a biological sample is measured, a signal of biological sample measuring sensor 11 inserted in sensor insertion section 1 is transmitted via connector section 16a to measurement section 7 disposed in control device 6. Thereafter, a biological sample (for example, blood, or the like) is measured (for example, blood glucose level is measured).

Install section 16 of main body case 2 may be integrated with substrate 4. Specifically, install section 16 may be configured in such a manner that a plurality of connection terminals configuring connector section 16a are provided to substrate 4 on which control device 6 is mounted.

Replaceable sensor insertion section 1 may be provided with other sensors than acceleration sensor 5a (such as temperature sensor and humidity sensor, for example) together with acceleration sensor 5a.

FIG. 10 illustrates a control block diagram of a biological sample measuring apparatus of the present embodiment. Different from the control block of Embodiment 1 and Embodiment 2 (FIG. 4), the control block illustrated in FIG. 10 includes two acceleration sensors 5a and 5b which are connected to determination section 9 of control device 6. A signal of acceleration sensor 5a is transmitted to determination section 9 via connector section 16a. Specifically, acceleration information (output information) of acceleration sensors 5a and 5b is input to determination section 9.

Since sensor insertion section 1 is replaceable in the biological sample measuring apparatus of the present embodiment, sensor insertion section 1 can be replaced when sensor insertion section 1 and its surrounding region are contaminated (for example, in the case where blood is adhered thereto). Thus, cleaning can be easily carried out, excellent serviceability and maintainability are advantageously achieved, biological sample measuring apparatus can be kept sanitary, and as a result, improvement in reliability (for example, stable operation of biological sample measuring apparatus) is achieved.

Embodiment 5

Figure 11:
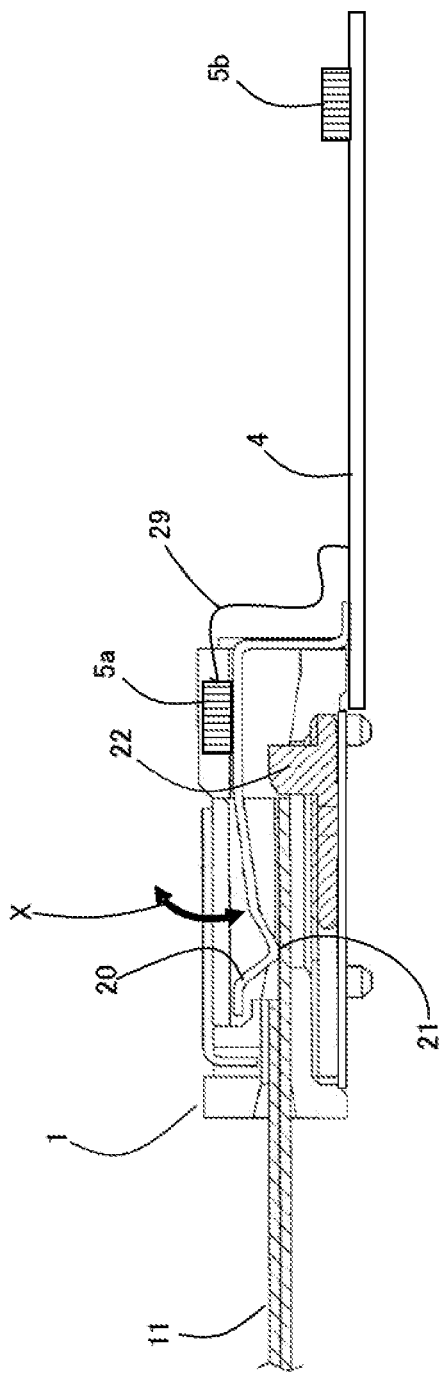
FIG. 11 is a sectional view illustrating the inside of a biological sample measuring apparatus according to Embodiment 5.

As illustrated in FIG. 11, in a biological sample measuring apparatus of the present embodiment, acceleration sensor 5a is provided in sensor insertion section 1, and acceleration sensor 5b is provided on substrate 4. FIG. 11 illustrates an internal sectional view of sensor insertion section 1 and its surroundings of the biological sample measuring apparatus of the present embodiment, and illustrates a state where biological sample measuring sensor 11 is inserted in sensor insertion section 1. A connection terminal (not illustrated) of biological sample measuring sensor 11 and contact section 21 of contact pin 20 are in contact with each other, and electrically connected to each other. It is to be noted that, in FIG. 11, portions corresponding to main electric circuits such as the control section are omitted for convenience.

Acceleration sensor 5a is disposed in contact with contact pin 20. In addition, acceleration sensor 5a is electrically connected to substrate 4 via wiring 29. The distal end (connection terminal) of biological sample measuring sensor 11 inserted in sensor insertion section 1 is locked at protrusion 22. That is, protrusion 22 functions as a stopper for biological sample measuring sensor 11. FIG. 11 illustrates a state where biological sample measuring sensor 11 is locked at protrusion 22, or in other words, a state where biological sample measuring sensor 11 is appropriately set in sensor insertion section 1.

The biological sample measuring apparatus in FIG. 8 includes acceleration sensor 5a which is a part of sensor insertion section 1 and is provided on substrate 4, whereas the biological sample measuring apparatus in FIG. 11 includes acceleration sensor 5a which is a part of sensor insertion section 1 and is attached so as to be in contact with contact pin 20.

When biological sample measuring sensor 11 is inserted in sensor insertion section 1, contact pin 20 is bent in an arrow X direction. Acceleration sensor 5a attached in contact with contact pin 20 detects an oscillation of contact pin 20. In this manner, the insertion of biological sample measuring sensor 11 can be detected by acceleration sensor 5a. Likewise, the ejection of biological sample measuring sensor 11 from sensor insertion section 1 can be detected by acceleration sensor 5a.

With the above-described configuration, at the time of the spot application of blood exuded from a finger on spot application section 11a of biological sample measuring sensor 11, acceleration sensor 5a can surely detect an impact caused when a "bending" state of biological sample measuring sensor 11 caused by the finger is forcefully cancelled, and/or an impact caused by the finger or the like making contact with biological sample measuring sensor during the measurement. When such an impact is detected, since it is highly possible that the measured value is unreliable, warning of a measurement defect can be displayed, without displaying the measured value.

When an impact is received during the measurement, the reagent in biological sample measuring sensor 11 and the like move from a given position, and thus an excessively small or excessively great measured value (blood glucose level) may be obtained erroneously. When the measured value is excessively small or excessively great, an inappropriate amount of insulin may be administered, and thus an accident may be caused. In particular, if the measured value is excessively small, then insulin is administered more than necessary based on the excessively small measured value, thus causing an accident leading to hypoglycemia which is a very dangerous condition. The blood measuring apparatus of the present invention can surely prevent such a problem.

After the installment of biological sample measuring sensor 11 in sensor insertion section 1 has been completed, blood or the like is spotted on spot application section 11a of biological sample measuring sensor 11 to start measurement. When the measurement is completed, results of the measurement are displayed on the display section. During the measurement, acceleration sensor 5a attached to contact pin 20 and acceleration sensor 5b provided on substrate 4 monitor whether an impact has been received from the outside. When an impact greater than a predetermined value is detected during the measurement, it is determined that the measured blood glucose level has a problem with the reliability. Then, without displaying the measured value, a warning indicating that "impact is caused during measurement, so measurement is failed" is displayed to urge a remeasurement.

More specifically, when each of acceleration sensor 5a and acceleration sensor 5b has detected an impact greater than a predetermined value, it is determined that the measuring apparatus itself has hit something and received an impact, and a measurement error message is displayed. Then, a warning which urges a confirmation whether the measuring apparatus itself can be operated.

When only acceleration sensor 5a has detected an impact greater than a predetermined value, it is determined that a finger or the like may have made contact with biological sample measuring sensor 11 during the measurement, and a measurement error message is displayed. Then, an attention message that urges a remeasurement and more careful operation is displayed.

After the measurement of blood glucose level and the like have been completed, the used biological sample measuring sensor 11 is pinched and pulled out by hand, and discarded. The impact caused by such an ejecting operation can be detected by acceleration sensor 5a. In this manner, acceleration sensor 5a can also detect both the insertion and ejection of sample measuring sensor 11.

The sensitivity of acceleration sensor 5a provided in sensor insertion section 1 and the sensitivity of acceleration sensor 5b on substrate 4 in FIG. 11 may cover respective measurement ranges different from each other. For example, the sensitivity of acceleration sensor 5a is about two to ten times higher than that of acceleration sensor 5b. As a more detailed example, it is conceivable to use an acceleration sensor covering a measurement range of −2 g to +2 g and another acceleration sensor covering a measurement range of −6 g to +6 g as acceleration sensors 5a and 5b, respectively. In this manner, the impact caused by making contact with the biological sample measuring sensor during the measurement can be measured with higher sensitivity, and thus the impact detection accuracy can be improved.

For the purpose of improving the reliability of measurement operation, the following threshold levels L1 to L3 may be set. The threshold level L1 is a threshold level for detecting the insertion and ejection of biological sample measuring sensor 11, and for example, may be set within the range of about 0.01 g to about 0.3 g. The threshold level L2 is a threshold level for detecting the fact that a finger or the like has made contact with the biological sample measuring sensor during the measurement (or a threshold level for detecting a possibility that the measured value lacks reliability), and for example, may cover a range of about 0.005 g to about 0.3 g. The threshold level L3 is a threshold level for determining that the measurement itself cannot be made, and for example, is desirably 0.5 g or more.

The relationships between threshold levels L1 to L3 are as follows, for example.

$$L1<L3 \quad (1)$$

$$L2<L3 \quad (2)$$

$$L1 \leq L2 \text{ or } L1 > L2 \quad (3)$$

Here, when the relationship between the threshold level L1 and threshold level L2 is set to L1>L2, even an impact (acceleration) smaller than the impact (acceleration) caused at the time of insertion or ejection of biological sample measuring sensor 11 is determined to be an error, and therefore high safety can be ensured.

In addition, the threshold levels L1 to L3 may be compared with acceleration data measured by both acceleration sensor 5a and acceleration sensor 5b; however, in terms of the purpose thereof, it is presumably more effective to compare the threshold level L1 and threshold level L2 mainly with acceleration data measured by acceleration sensor 5a provided in sensor insertion section 1, and to compare the threshold level L3 with acceleration data measured at acceleration sensor 5b provided on substrate 4. In view of the foregoing, acceleration sensors having sensitivities different from each other may be selected for acceleration sensor 5a and acceleration sensor 5b as described above.

Preferably, acceleration sensor 5a attached in sensor insertion section 1 (on contact pin 20 in FIG. 11), and acceleration sensor 5b disposed on substrate 4 in the apparatus are each a three-dimensional acceleration sensor.

Figure 12A:
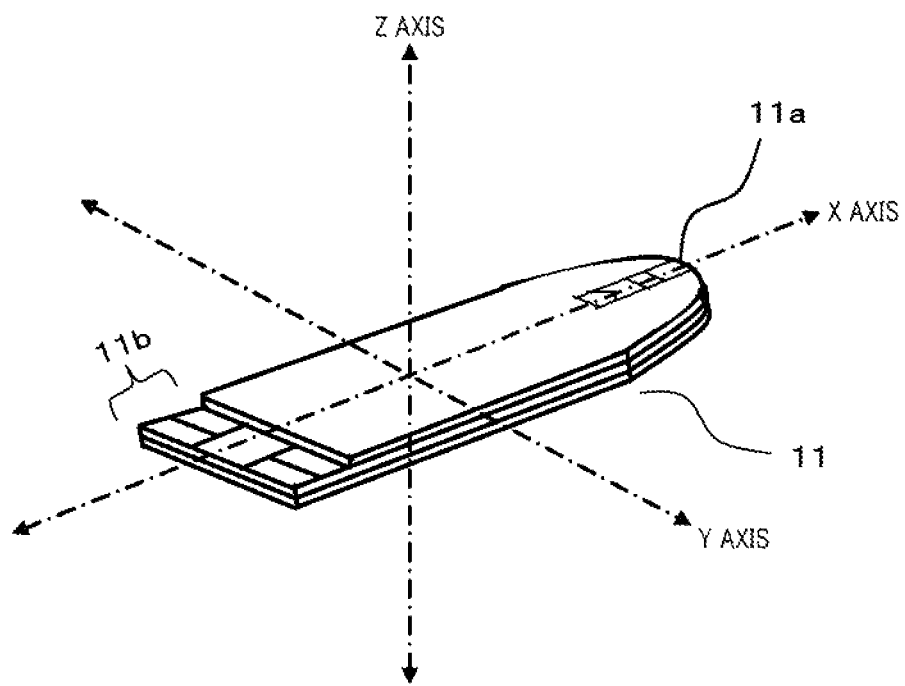
FIG. 12A illustrates relationships between axes of a three-dimensional acceleration sensor and a biological sample measuring sensor.

FIG. 12A illustrates a relationship between axes of three-dimensional acceleration sensor (X axis, Y axis, and Z axis) and the biological sample measuring sensor. In FIG. 12A, the X axis is in parallel to the longitudinal direction of plate-shaped biological sample measuring sensor 11, the Y axis is orthogonal to the X axis, and the Z axis is orthogonal to the X axis and Y axis, that is, perpendicular to the X-Y plane. This relationship is merely an example, and it is only necessary that all of the plurality of acceleration sensors are so set as to have the same standard axis. Specifically, while the direction in parallel to the longitudinal direction of the biological sample measuring sensor is defined as the X axis serving as the standard axis in FIG. 12A, the direction in parallel to the longitudinal direction of the biological sample measuring sensor may be defined as the Y axis serving as the standard axis, or alternatively, the direction in parallel to the longitudinal direction of biological sample measuring sensor may be defined as the Z axis serving as the standard axis. In other words, it is only necessary that the three-dimensional acceleration sensors are so set as to have a common (same) X axis, Y axis, and Z axis.

Figure 12B:
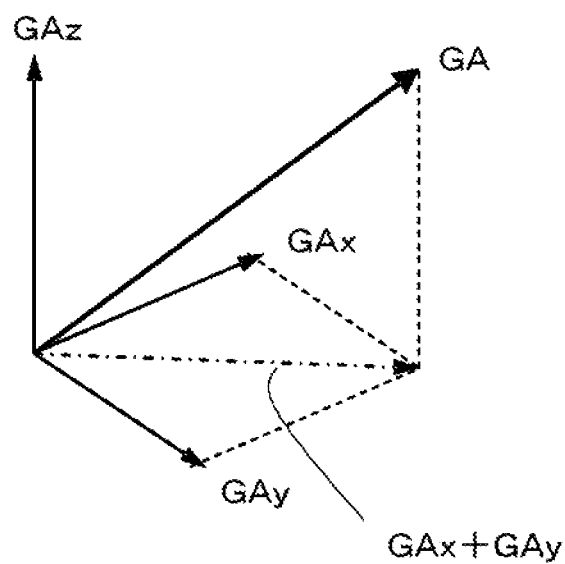
FIG. 12B illustrates vector components of a measured acceleration.

The following description explains a measured acceleration GA and a measured acceleration GB respectively measured by three-dimensional acceleration sensor 5a and three-dimensional acceleration sensor 5b illustrated in FIG. 12A. The accelerations GA and GB are expressed as follows. Here, the accelerations GA and GB each represent a vector value showing the direction and magnitude as illustrated in FIG. 12B. In the expression, GAx, GAy, and GAz represent x, y, and z components of GA, respectively. Likewise, GBx, GBy, and GBz represent x, y, and z components of GB, respectively (the same shall apply hereinafter).

GA=GAx+GAy+GAz (this expresses the vectorial sum of X-, Y-, and Z-axis components)

GB=GBx+GBy+GBz (this expresses the vectorial sum of X-, Y-, and Z-axis components)

The measured accelerations GA and GB are defined as follows according to when the measurement is made.

Accelerations measured at the time of insertion of biological sample measuring sensor 11 in sensor insertion port 1: GA1, GB1

Accelerations measured while blood glucose level is being measured: GA2, GB2 (each of the measured accelerations GA2 and GB2 is not limited to one, and, normally, measured multiple times)

Accelerations measured at the time of ejection of biological sample measuring sensor 11 from sensor insertion port 1: GA3, GB3

Determination can be made as follows based on measured accelerations GA2 and GB2. When measured accelerations GA2 and GB2 cannot be obtained, it is determined that the biological sample measuring apparatus itself is an error (broken). When "measured accelerations GA2 and GB2>threshold level L3", it is determined that the biological sample cannot be measured, and confirmation whether the measuring apparatus is broken and remeasurement are requested. When "threshold level L3>measured accelerations GA2 and GB2>threshold level L2", it is determined that the measurement may not have appropriately made, and replacement of the biological sample measuring sensor and remeasurement are requested. When "measured accelerations GA2 and GB2≤threshold level L2", it is determined that the measurement has been appropriately made.

Naturally, it is also possible to compare only the measured accelerations GA2 with threshold level L2 to determine whether the measurement has been made appropriately. In addition, when acceleration sensors 5a and 5b have different sensitivities, measured accelerations GA2 and GB2 obtained by subjecting data received from acceleration sensors 5a and 5b to sensitivity conversion are compared with threshold levels L2 and L3, respectively. The sensitivity conversion is carried out by determination section 9 or control section 8 (see FIG. 10, for example).

In addition, determination can also be made as follows based on X-, Y-, and Z-axis components (measured acceleration components) of measured accelerations GA2 and GB2. When "measured acceleration components GA2x, GA2y, GA2z, GB2x, GB2y or GB2z>threshold level L3", it is determined that an impact is received during the measurement of blood glucose level, and therefore blood glucose level cannot be measured. When "measured acceleration component GB2z (GB2x, or GB2y)>threshold level L2", it is determined that an impact is received during the measurement, and therefore blood glucose level may have not been appropriately measured. When "measured acceleration component GA2x, GA2y, GA2z, GB2x, GB2y and GB2z≤threshold level L2", it is determined that the measurement has been appropriately made.

Figure 12C:
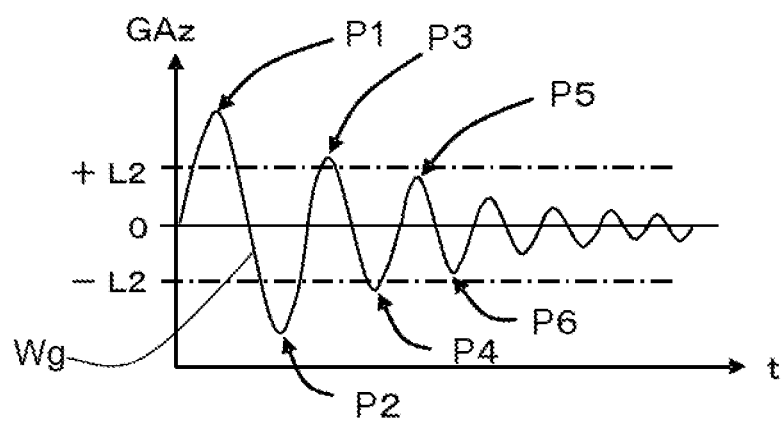
FIG. 12C illustrates an exemplary waveform of a signal output from the acceleration sensor.

The following specifically describes the case where the biological sample measuring sensor is flicked by a finger or the like. FIG. 12C illustrates an exemplary output signal waveform Wg in a Z-axial direction, which is one of signals output from three-dimensional acceleration sensor 5a when a finger or the like makes contact with biological sample measuring sensor 11 during the measurement of blood glucose level. Here, in consideration of the positional relationship of the sensor insertion section and the contact pin, a case is studied in which a significant movement is caused in a vertical direction relative to the planer face of biological sample measuring sensor 11, that is, in the Z-axial direction.

When a finger or the like makes contact with biological sample measuring sensor 11, or when biological sample measuring sensor 11 is released from a bending state, an output signal Wg in a form of an oscillation waveform in FIG. 12C is output from acceleration sensor 5a. Specifically, the value of the measured acceleration of GAz largely oscillates up and down (that is, in the positive/negative direction) with respect to the center: 0, and attenuates as time t passes.

The data of the output signal Wg representing the change of the value of the measured acceleration in the Z-axial direction is retrieved at determination section 9 from three-dimensional acceleration sensor 5a, and stored in memory section 10. The pieces of measured acceleration data of acceleration sensor 5a and the threshold level L2 are compared, and it is determined at determination section 9 whether the threshold level L2 is exceeded. To be more specific, initial peak values of the Z-axis output signal Wg (P1, P3, P5 and the like as the positive peak values and P2, P4, P6 and the like as the negative peak values) are obtained, and the values thus obtained are compared with the threshold level L2 for determination during the measurement of acceleration sensor 5a. Then, when the peak value P1 is greater than the positive threshold level L2 (+L2), and/or when the peak value P2 is smaller than the negative threshold level L2 (−L2), it is determined to be an error.

In addition, it is seen from the example of FIG. 12C that the output signal Wg includes positive peak values P1 and P3 which are greater than the threshold level +L2, and has a form of an oscillation waveform. Likewise, the output signal Wg includes negative peak values P2 and P4 which are lower than the threshold level −L2, and has a form of an oscillation waveform. As described, since a plurality of peak values are detected and an oscillation waveform is confirmed, it is recognized that the error has been caused by "a finger or the like making contact with the biological sample measuring sensor", not by dropping of the measuring apparatus or clashing of the measuring apparatus with external objects.

On the other hand, in the case of "dropping of the measuring apparatus or clashing of the measuring apparatus with external objects", the oscillation waveform illustrated in FIG. 12C is not obtained, and only one peak value is typically shown. Specifically, not the waveform whose peak value gradually attenuates as time passes as illustrated in FIG. 12C, but a waveform whose large peak value abruptly attenuates after the peak value is caused at the time of the impact as illustrated in FIG. 12D is typically obtained.

Figure 12D:
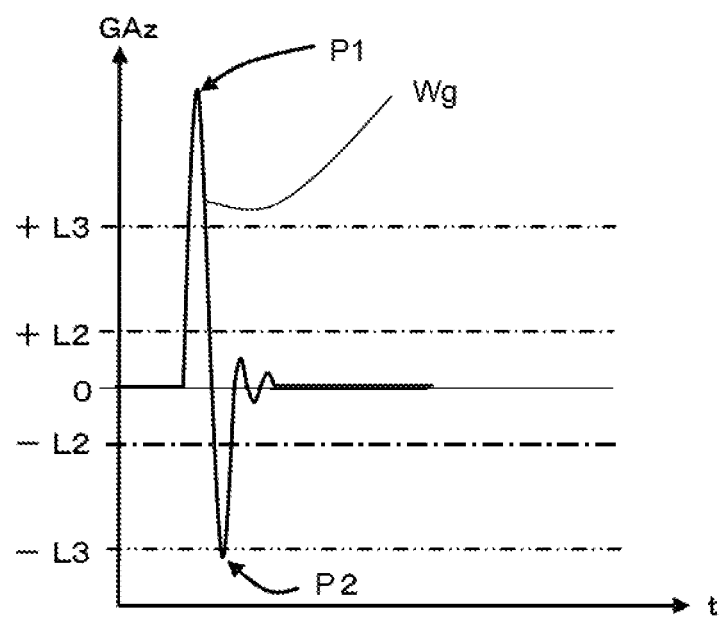
FIG. 12D is another exemplary waveform output from the acceleration sensor.

FIG. 12D illustrates an exemplary output signal Wg of the Z-axis component of three-dimensional acceleration sensor 5a in the case of "dropping of the measuring apparatus or clashing of the measuring apparatus with external objects." In the example of FIG. 12D, peak P1 at the time of the impact has a high peak value exceeding not only the threshold level +L2 but also the positive threshold level L3 (+L3: the threshold level L3 is "a threshold level at which the measurement itself is determined to be impossible"). Specifically, errors are discriminated from each other by comparison between the threshold level L3 (+L3) and a peak value P1 in the measured acceleration data of the Z-axis component of the measured acceleration GA (or GA2 during the measurement) of capacitance-type three-dimensional acceleration sensor 5a. In other words, discrimination according to the magnitude of the impact can be made. Likewise, when a value of the peak P2 which is the maximum value on the negative side is lower than the negative threshold level L3 (−L3), it is determined that the error has been caused possibly by "dropping of the measuring apparatus or clashing of the measuring apparatus with external objects."

While FIG. 12D illustrates an exemplary case where both of the peak values of P1 and P2 are greater than the threshold level L3, this is not limitative. Alternatively, only peak P1 may be greater than the threshold level L3, or only peak P2 may be greater than the threshold level L3. This is because the impact is applied with variety of intensities and directions, and therefore cannot be limited to a single type of impact. Accordingly, it is necessary to compare the threshold levels (+L3, −L3, and the like) with the peak values on the positive side and negative side.

In addition, the error of FIG. 12D can be discriminated from the error caused by "a finger or the like making contact with biological sample measuring sensor" based on the fact that the oscillation waveform as illustrated in FIG. 12C is not obtained in the case of FIG. 12D.

As described above, since the output signal Wg from the acceleration sensors is monitored in the present invention, it is possible to discriminate not only the magnitudes of the impact, but also the causes of the impact by checking the waveform of the output signals Wg (by checking whether an oscillation waveform is obtained, for example). Consequently, an instruction, display, and notification of caution and warning can be correctly presented to the user at the time of the biological sample measurement, and thus, the safety and reliability of the measuring apparatus are improved.

While FIG. 12C illustrates an example of a gradually attenuating oscillation waveform, the form of the waveform is not limited to this. Also in the case of the oscillation waveform illustrated in FIG. 12C, factors such as the peak values, the frequency or cycle of the oscillation, and the attenuation time may vary, and therefore various waveforms may be obtained. Further, not the oscillation waveform, but a momentary waveform may be observed in the case where the measuring apparatus is dropped and the like. As described, the impact is applied to the measuring apparatus from the outside in various manners, and therefore various waveform patterns are conceivable.

When an impact has been applied in a direction substantially parallel to the X, Y, or Z axial direction, the measured acceleration component can be compared with the threshold level L2 or L3. Meanwhile, when an impact is applied in a direction not parallel to the X, Y, or Z axial direction, there is a difference between components along respective axes (GB2x, GB2y, GB2z, and the like) and synthesized vector values (GA2, GB2, and the like, see FIG. 12B). Therefore, the determination can be made more accurately not only by comparing the components of the measured acceleration (GB2x, GB2y, GB2z, and the like) with the threshold levels L1 to L3, but also by comparing the synthesized measured accelerations GA2 and GB2 with the threshold levels L1 to L3.

Embodiment 6

Figure 13:
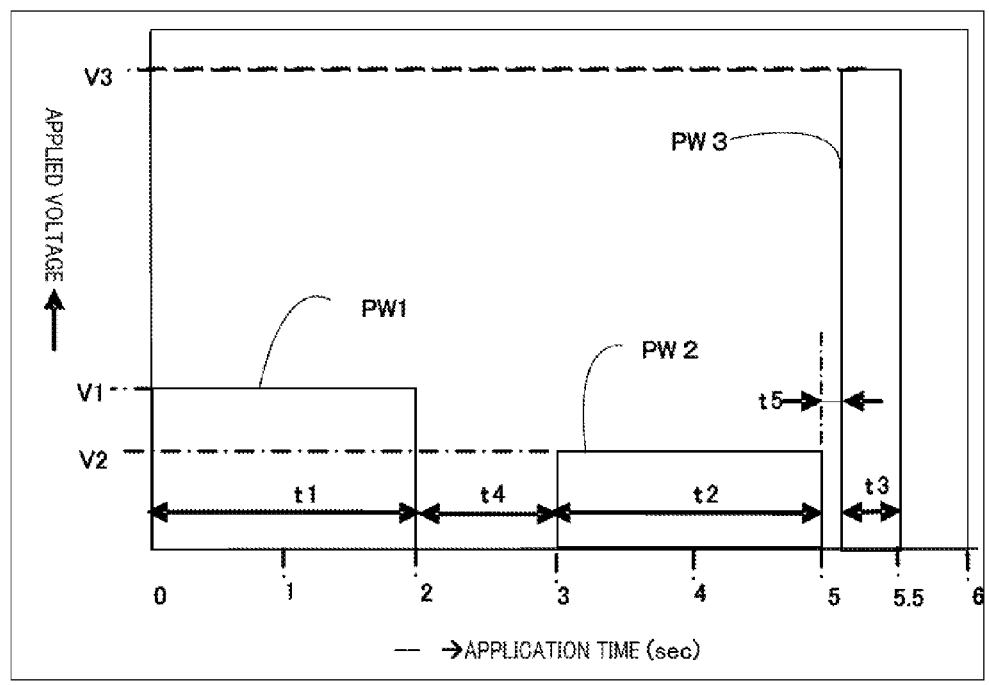
FIG. 13 is a graph illustrating a waveform pattern of an applied voltage for use in a blood glucose level measurement in a biological sample measuring apparatus according to Embodiment 6.

FIG. 13 illustrates an exemplary waveform pattern of an applied voltage for use in the blood glucose level measurement. Here, measurement timings of the acceleration sensor are described. FIG. 13 illustrates a waveform of an applied voltage supplied from the measuring apparatus to the detection electrode (electrode for the measurement such as a working electrode and counter electrode) of the biological sample measuring sensor for the purpose of measuring blood glucose levels (glucose level). FIG. 13 illustrates the case where multi (three)-pulse waveforms (rectangular waves) are applied.

To be more specific, as pulse PW1, a voltage V1 (e.g., 350 mV or a voltage in the range of 100 to 800 mV can be adopted) is applied for a time t1 (e.g., for two seconds, or about 0.5 seconds to about 5 seconds) from the start of the measurement. A voltage is not applied for a time t4 (e.g., for one second or about 0.1 second to about 3 seconds) subsequent to the time t1. Next, as a pulse PW2, a voltage V2 (e.g., 250 mV or a voltage in the range of 100 to 800 mV can be adopted) is again applied for a time t2 (e.g., for two seconds or 0.5 to 5 seconds). A voltage is not applied for a time t5 (e.g., for 0.1 second, or 0 to 0.1 second) subsequent to the time t2. Further, as a pulse PW3, a voltage V3 (e.g., 2.5 V or 1.5 to 3.5 V) is applied for a time t3 (e.g., for 0.5 seconds or 0.1 to 2 seconds).

Here, the pulse PW1 and pulse PW2 each represent a voltage application for measuring a glucose level, or a voltage application for measuring interfering substances (substances that have influence on the glucose level measurement). Meanwhile, the pulse PW3 represents a voltage application for measuring an Hct (hematocrit) level.

Figure 14:
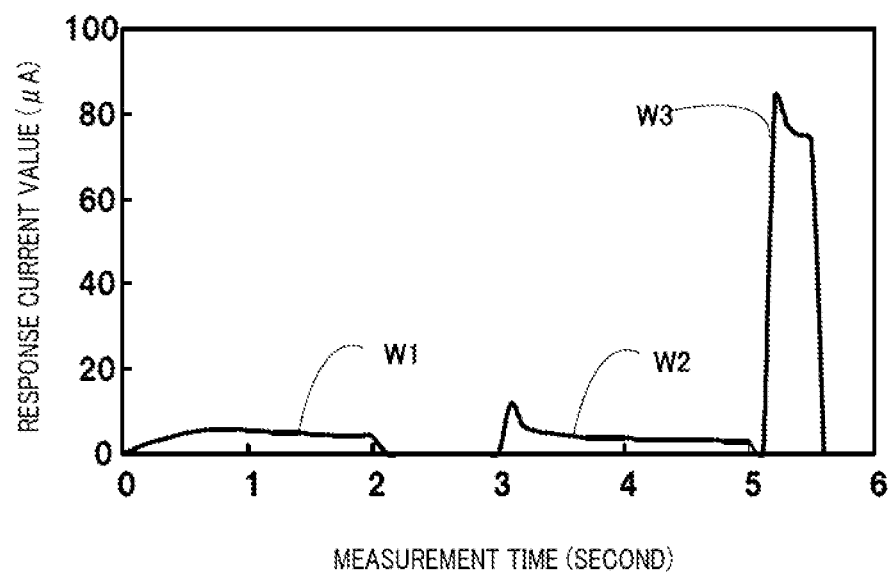
FIG. 14 is a graph illustrating a signal output from a detection electrode of the biological sample measuring sensor when the voltage waveform pattern illustrated in FIG. 13 is applied thereto.

In addition, FIG. 14 illustrates signals output from the detection electrode (a working electrode and a counter electrode, for example) of the biological sample measuring sensor at the time of a blood glucose level measurement, for example, upon application of the pulse voltages illustrated in FIG. 13. W1 represents a signal output from the detection electrode (a working electrode and a counter electrode, for example) upon application of the pulse voltage PW1 (applied voltage V1 and applied time t1). W2 represents an output signal upon application of the pulse voltage PW2 (applied voltage V2 and applied time t2). These signals are output signals corresponding to reaction currents generated by redox reactions in the biological sample measuring sensor, that is, glucose levels. Meanwhile, W3 represents a signal output from an Hct electrode upon application of the pulse voltage PW3 (applied voltage V3 and applied time t3). That is, an output signal corresponding to an Hct level. Based on the glucose level, Hct (hematocrit) level, and other data (temperature data, data of interfering materials, and the like), a glucose level (blood glucose level) at a standard temperature is determined.

When an impact is applied to the measuring apparatus from the outside while the glucose level is being measured in the above-mentioned manner, a reagent dissolved with blood in the reaction deviates from a given position (for example, on the detection electrode), appropriate reaction may not be sufficiently caused, and thus the measured value of the glucose level may not be accurate or the measurement itself may not be made. The above-mentioned case where "impact is applied to the measuring apparatus" includes the case where an impact is applied to the measuring apparatus from the outside, the case where the measuring apparatus is dropped, the case where a finger makes contact with the biological sample measuring sensor, the case where a finger is strongly pressed against the biological sample measuring sensor such that the sensor is deflected when blood is spotted on the biological sample measuring sensor, and the like.

To solve this problem, the acceleration sensor incorporating the measuring apparatus is used. Specifically, when whether an impact is caused during the measurement is accurately detected, and an impact is detected during the measurement, the measured data is determined to be inaccurate. Therefore, the measured data is not displayed, but an error message is displayed to urge a remeasurement and the like. As a result, only reliable measured values are displayed on the display section, and thus the reliability as a measuring apparatus is improved.

Figure 15:
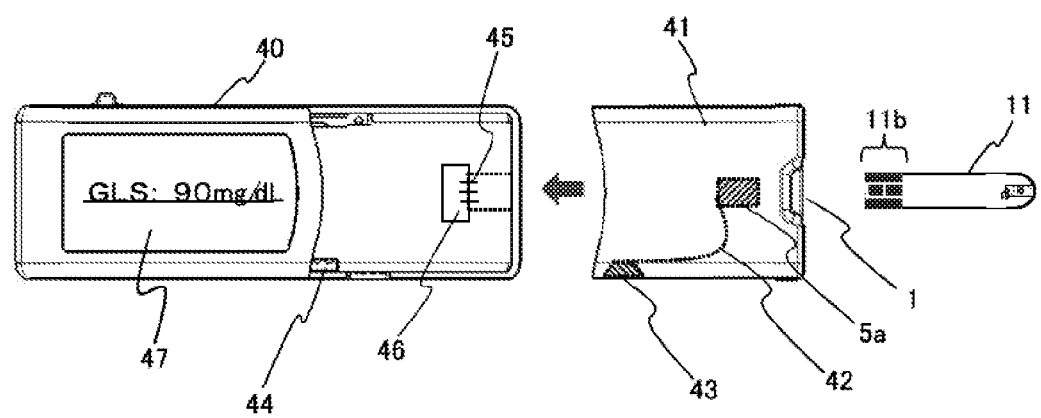
FIG. 15 is a plan view of a biological sample measuring apparatus according to Embodiment 7.

In addition, when an impact is received during the application of the pulse voltage PW1, PW2 or PW3, also the output signal W1, W2 or W3 in FIG. 15 typically has an abnormal waveform. Accordingly, the impact can also be detected based on the waveform of the output signal W1, W2 or W3. However, the signals are not output during a time period in which a voltage is not applied (time periods t4 and t5 in FIG. 13) and immediately before the start of the measurement (before a voltage is applied), and therefore it is difficult to detect an impact based on the output signal waveform. Hence the detection using the acceleration sensor is important.

While FIG. 13 and FIG. 14 illustrate the case where the applied voltage has a multiple waveform including three waveforms of PW1, PW2, and PW3, similar effects can be obtained with a multiple waveform including two waveforms (when the voltage application for the Hct value measurement is not carried out), and with a multiple waveform including four or more waveforms (three or more voltage applications for the glucose measurement). As described above, in the present invention, an impact caused during the blood glucose level measurement can be surely detected regardless of the timing. Consequently, although an accident leading to hypoglycemia which is a very dangerous condition has been caused in the past when the measured value is excessively small due to the impact applied from the outside and insulin is administered more than necessary based on the excessively small measured value, such an accident can be precluded by displaying only highly-reliable measured values on the display section. Thus, the reliability and safety of the measuring apparatus are further ensured.

Embodiment 7

FIG. 15 illustrates a modification of the biological sample measuring apparatus for blood glucose level measurement and the like in FIG. 9 and FIG. 10, and illustrates a biological sample measuring apparatus including measuring apparatus main body 40 having display section 47, and cover 41 for covering part of measuring apparatus main body 40. Cover 41 is provided with sensor insertion section 1 for insertion of biological sample measuring sensor 11, and further, acceleration sensor 5a on a rear surface thereof.

Acceleration sensor 5a provided on the rear surface of cover 41 is electrically connected to electric circuits of the control section and the like incorporated in main body 40 via wiring 42, connecting section 43, connecting section 44 of main body when cover 41 is installed to measuring apparatus main body 40. Thus, power is supplied to acceleration sensor 5a from apparatus main body 40 by way of connecting section 44 and/or the like when cover 41 is installed to apparatus main body 40, and in addition, a signal from acceleration sensor 5a can be sent to the apparatus main body 40.

In addition, biological sample measuring sensor 11 makes contact with connection electrode section 11b (which is connected to detection electrodes for measurement such as a working electrode and a counter electrode) of biological sample measuring sensor 11, and a plurality of contact pins 45 disposed at sensor contact section 46 of measuring apparatus main body 40, thereby establishing an electrical connection to the electric circuits of the measurement section and the like in measuring apparatus main body 40.

When acceleration sensor 5a is provided to replaceable cover 41 in the biological sample measuring apparatus illustrated in FIG. 15, acceleration sensors having different sensitivities can be used by replacing cover 41. As an additional sensor, acceleration sensor 5b (not illustrated) may be provided on substrate 4 of measuring apparatus main body 40. By making the sensitivities of the two acceleration sensors 5a and 5b different from each other, impacts of different magnitudes can be detected. Consequently, the impact caused when biological sample measuring sensor 11 is touched is detected with high sensitivity, and thus it is possible to improve the detection performance during the measurement and to achieve more reliable measurement and a more reliable measuring apparatus.

Embodiment 8

Figure 16:
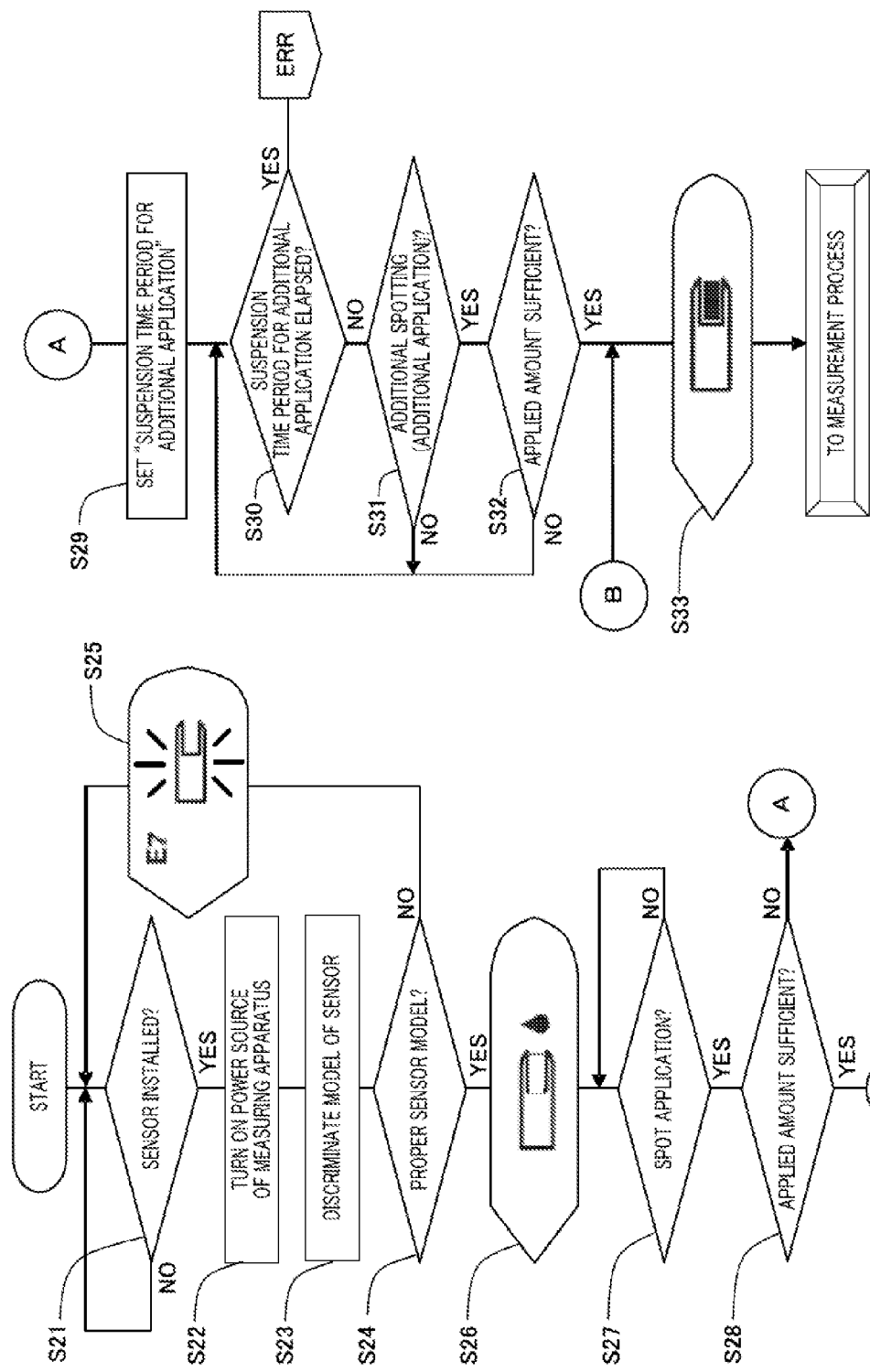
FIG. 16 is a flowchart explanatory of a measurement operation including additional spotting in a biological sample measuring apparatus according to Embodiment 8.

When the amount of the biological sample spotted on biological sample measuring sensor 11 is excessively small, the measurement of the amount of the biological component (e.g., blood glucose level measurement and the like) cannot be made appropriately. In that case, the measurement is occasionally made after additionally spotting (also referred to as "additional application") the biological sample. Therefore, in some cases, it is necessary to wait for a certain time period until an additional spot application is received after the amount of the biological sample spotted thereto is determined to be excessively small. FIG. 16 illustrates an operational flow in which whether "additional application" as the above-mentioned additional spotting has been carried out is detected by acceleration sensor 5a and/or the like. In the operational flow illustrated in FIG. 16, the additional application is detected by acceleration sensor 5a disposed in sensor insertion section 1 (see FIG. 11, for example). In the following, steps S21 to S33 are described in detail.

S21: The installment of biological sample measuring sensor 11 is confirmed. Whether biological sample measuring sensor 11 is installed to sensor insertion section 1 (see FIG. 11, for example) is confirmed by confirming the conduction/resistance value between terminals of contact section 16a on the measuring apparatus (a plurality of contact pins 20, see FIG. 9, FIG. 15, for example) that makes contact with connection electrode section 11b (see FIG. 12, for example) of biological sample measuring sensor 11. When the installment of biological sample measuring sensor 11 is confirmed, the process is advanced to step S22.

S22: When the installment of biological sample measuring sensor 11 has been confirmed, a main power source of measuring apparatus is turned ON. Thus, display section 3 (see FIG. 1, for example) and/or the like is allowed to perform display. It is to be noted that the main power source may be turned ON by pushing a power source button of measuring apparatus.

S23: The model of installed biological sample measuring sensor 11 is determined. The model determination is carried out based on the difference of a pattern and the like provided at connection electrode section 11b of biological sample measuring sensor 11.

S24: When the model thus determined is not a proper model, the process is advanced to step S25, whereas when the model thus determined is a proper model, the process is advanced to step S26.

S25: A model error message (in FIG. 16, error code "E7") is displayed, and an instruction to replace biological sample measuring sensor 11 with a proper model is issued. Then, the process is returned to S21.

S26: A message that urges "spot application of blood" is displayed to urge the user to spot blood on biological sample measuring sensor 11.

S27: Whether blood has been spotted on spot application section 11a of biological sample measuring sensor 11 is determined. To confirm spot application of blood, a plurality of "detection electrodes" are provided along a flow direction of blood, and change in resistance value and the like are detected between the detection electrodes when inflow of blood occurs. For example, at first, spot application is detected at a first detection electrode nearest spot application section 11a of biological sample measuring sensor 11. When spot application of blood has been confirmed, the process is advanced to step S28.

Alternatively the spot application of blood may be indirectly detected by acceleration sensor 5a (see FIG. 11, for example). Specifically, when a user spots blood exuded from a finger on spot application section 11a disposed at an end of biological sample measuring sensor 11, the finger naturally makes contact with biological sample measuring sensor 11. The contact thus made can be detected at acceleration sensor 5a. In that case, it is only necessary to detect the contact between the finger and biological sample measuring sensor 11.

The manner of bringing a finger into contact with spot application section 11a of biological sample measuring sensor 11 for spot application of blood varies from user to user. Some users strongly press spot application section 11a with a finger, while others softly make contact with spot application section 11a with a finger. Accordingly, it is preferable that the threshold level L4 for detecting a contact between the finger and the biological sample measuring sensor be smaller than the threshold level L2 for determining the impact during the measurement. It suffices that $L4 \leq L2$, but preferably, $L4=\alpha*L2$ ($\alpha$=about 1/1 to about 1/10). It suffices to set the threshold level L4 at about 0.005 g to about 0.3 g for example.

S28: Whether blood has sufficiently flowed into a capillary of sensor 11a (supply path not illustrated) is detected at a second detection electrode (detection electrode disposed at a position farthest from spot application section 11a). When inflow of blood is detected, it is determined that a sufficient amount of blood required for measurement has flowed into the capillary (supply path) of biological sample measuring sensor 11, and the process is advanced to step S33. Meanwhile, when inflow of blood is determined to be insufficient, the process is advanced to step S29. It is preferable that the second detection electrode be disposed at a position farthest from spot application section 11a, but it suffices that the second detection electrode is disposed on the depth side of the capillary relative to the detection electrodes such as a working electrode and counter electrode for detecting an oxidation-reduction reaction current (distal side from spot application section 11a).

S29: In a sequence of additional spotting (additional application) of biological sample, a time period (suspension time period for additional application) during which the operation is suspended until "additional application (additional spotting)" is received is set. Preferably, the additional application suspension time is, for example, about 10 seconds to about 120 seconds, preferably, 15 to 60 seconds.

S30: The suspension time period for additional application is monitored, and the lapse of the suspension time period, if any, is determined to be an error as "spotting defect"/"insufficient spotting amount". Then an error message is displayed on display section 3 and a warning sound is output by a sounder to urge replacement of biological sample measuring sensor 11 and remeasurement.

S31: Whether the user's finger has made contact with spot application section 11a is detected by acceleration sensor 5a (see FIG. 11, for example) to determine whether additional spotting has been carried out on biological sample measuring sensor 11. Basically, step 31 is similar to step S27, and the threshold level L4 is set as in the case of step S27. When the additional spotting is detected, the process is advanced to step S32. When additional spotting cannot be detected, the process is returned to step S30.

S32: Similarly to the above-mentioned step S28, inflow of blood is detected according to change in resistance value and the like between the second detection electrode disposed at a position farthest (most distant in the depth direction) from spot application section 11a and a predetermined electrode. When blood is detected, it is determined that blood sufficient for measurement has flowed into the capillary (supply path) of biological sample measuring sensor 11, and the process is advanced to step S33. When it is determined that the blood is insufficient, the process is returned to step S30.

S33: When the spot application amount (the amount of a sample (specimen) such as blood) is sufficient and it is determined that the measurement can be made, a message "spot application is completed" is displayed, and then blood glucose level is measured.

INDUSTRIAL APPLICABILITY

As described above, the present invention includes a main body case including a sensor insertion section; a measurement section connected to the sensor insertion section; a control section connected to the measurement section; and a display section connected to the control section, wherein an acceleration sensor that detects an impact applied to the sensor insertion section is provided. Thus, the reliability of measured value and measurement accuracy can be improved.

Specifically, in the present invention, the acceleration sensor detects an impact applied to the sensor insertion section via a biological sample measuring sensor, for example. When the impact detected by the acceleration sensor is greater than a predetermined value, it is possible to determine the measurement result measured by the measurement section to be inadequate, and to display, on the display section, the fact that the measurement result is inadequate without displaying the measured value. Therefore, an inadequate measurement result with unreliability is prevented from being displayed, and improvement in measurement accuracy is achieved. Consequently, utilization of a biological sample measuring apparatus of the present invention as a biological sample measuring apparatus for measuring blood glucose levels, lactate level, and the like is anticipated.

REFERENCE SIGNS LIST

1 Sensor insertion section
2 Main body case
3 Display section
4 Substrate
5, 5a, 5b Acceleration sensor
6 Control device
7 Measurement section
8 Control section
9 Determination section
10 Memory section
11 Biological sample measuring sensor
11a Spot application section
12 Insertion detection section
13 Buzzer
14, 15 Operation button
16 Install section
16a Connector section
20 Contact pin
21 Contact section
22 Protrusion
29 Wiring
40 Measuring apparatus main body
41 Cover
42 Wiring
43 Connecting section
44 Connecting section
45 Contact pin
46 Sensor contact section
47 Display section

The invention claimed is:

1. A biological sample measuring apparatus comprising:
a main body case including a sensor insertion section;
a measurement section connected to the sensor insertion section;
a control section connected to the measurement section; and
a display section connected to the control section, wherein
the sensor insertion section includes a contact pin that is configured to make contact with an electrode of a biological sample measuring sensor when the biological sample measuring sensor is inserted in the sensor insertion section, and an acceleration sensor disposed in contact with the contact pin,
the contact pin is bendable so as to oscillate,
an oscillation of the biological sample measuring sensor is configured to be transmitted to the acceleration sensor via the contact pin, and
the acceleration sensor is configured to detect an impact applied to the sensor insertion section.

2. The biological sample measuring apparatus according to claim 1 further comprising:
a determination section connected to the acceleration sensor, the determination section detecting a signal output from the acceleration sensor upon application of an impact; and
a memory section connected to the determination section, wherein
the determination section and the memory section are connected to the control section.

3. The biological sample measuring apparatus according to claim 1, wherein the acceleration sensor is a three-dimensional acceleration sensor.

4. The biological sample measuring apparatus according to claim 1, further comprising a second acceleration sensor.

5. The biological sample measuring apparatus according to claim 4, wherein
at least one of the acceleration sensor and the second acceleration sensor is a three-dimensional acceleration sensor.

6. The biological sample measuring apparatus according to claim 4, wherein
the measurement section and the control section are disposed on an electric circuit substrate in the main body case,
the second acceleration sensor is disposed on the electric circuit substrate in the proximity of the sensor insertion section.

7. The biological sample measuring apparatus according to claim 4, wherein
when each of the acceleration sensor and the second acceleration sensor has detected an impact greater than a predetermined value, the display section displays a warning message that urges a confirmation whether or not the biological sample measuring apparatus can be operated.

8. The biological sample measuring apparatus according to claim 4, wherein
when only the acceleration sensor has detected an impact greater than a predetermined value, the display section displays an attention message that urges more careful operation.

9. The biological sample measuring apparatus according to claim 4, wherein
sensitivity of the acceleration sensor is higher than that of the second acceleration.

10. The biological sample measuring apparatus according to claim 1, wherein
the acceleration sensor detects an impact of ejecting operation to discard the used biological sample measuring sensor.

11. A biological sample measuring apparatus comprising:
a main body case including a sensor insertion section;
a measurement section connected to the sensor insertion section;
a control section connected to the measurement section; and
a display section connected to the control section, wherein
the sensor insertion section includes a contact pin that is configured to make contact with an electrode of a biological sample measuring sensor when the biological sample measuring sensor is inserted in the sensor insertion section, and an acceleration sensor disposed at a position adjacent to the contact pin;
the contact pin is bendable so as to oscillate;
an oscillation of the biological sample measuring sensor is configured to be transmitted to the acceleration sensor via the contact pin; and
the acceleration sensor that is configured to detect an impact applied to the sensor insertion section.

12. The biological sample measuring apparatus according to claim 11 further comprising:
a determination section connected to the acceleration sensor, the determination section detecting a signal output from the acceleration sensor upon application of an impact; and
a memory section connected to the determination section, wherein
the determination section and the memory section are connected to the control section.

13. The biological sample measuring apparatus according to claim 11, wherein
the acceleration sensor is a three-dimensional acceleration sensor.

14. The biological sample measuring apparatus according to claim 11, further comprising a second acceleration sensor.

15. The biological sample measuring apparatus according to claim 14, wherein
at least one of the acceleration sensor and the second acceleration sensor is a three-dimensional acceleration sensor.

16. The biological sample measuring apparatus according to claim 14, wherein
the measurement section and the control section are disposed on an electric circuit substrate in the main body case,
the second acceleration sensor is disposed on the electric circuit substrate in the proximity of the sensor insertion section.

17. The biological sample measuring apparatus according to claim 14, wherein
when each of the acceleration sensor and the second acceleration sensor has detected an impact greater than a predetermined value, the display section displays a warning message that urges a confirmation whether or not the biological sample measuring apparatus can be operated.

18. The biological sample measuring apparatus according to claim 14, wherein
when only the acceleration sensor has detected an impact greater than a predetermined value, the display section displays an attention message that urges more careful operation.

19. The biological sample measuring apparatus according to claim 14, wherein sensitivity of the acceleration sensor is higher than that of the second acceleration.

20. The biological sample measuring apparatus according to claim 11, wherein
the acceleration sensor detects an impact of ejecting operation to discard the used biological sample measuring sensor.

* * * * *